United States Patent [19]
Larsky et al.

[11] Patent Number: 5,569,368
[45] Date of Patent: Oct. 29, 1996

[54] ELECTROPHORETIC APPARATUS AND METHOD FOR APPLYING THERAPEUTIC, COSMETIC AND DYEING SOLUTIONS TO HAIR

[76] Inventors: Edvin G. Larsky, 2240 Wilson Blvd., Apt. No. 5, Winchester, Va. 22601; Gary Van Sickler, 342 Light Rd., Winchester, Va. 22603

[21] Appl. No.: 463,806

[22] Filed: Jun. 5, 1995

Related U.S. Application Data

[62] Division of Ser. No. 369,446, Jan. 6, 1995, Pat. No. 5,472,456.

[51] Int. Cl.$^6$ .......................... G01N 27/26; A45D 19/02
[52] U.S. Cl. .......................... 204/600; 204/450; 205/691; 132/148; 132/202; 132/208; 8/444
[58] Field of Search .................................... 205/687, 688, 205/689, 690, 691, 701; 204/450, 600; 132/208, 202, 241, 207, 208, 219, 148; 8/444

[56] References Cited

U.S. PATENT DOCUMENTS 1,724,984  8/1929  Wildey ........................................ 132/148
5,072,746  12/1991  Kantor ..................................... 132/271 X

*Primary Examiner*—Kathryn Gorgos
*Assistant Examiner*—John S. Starsiak, Jr.
*Attorney, Agent, or Firm*—Morgan & Finnegan

[57] ABSTRACT

A method of introducing therapeutic, cosmetic, and dyeing agents in buffer medium created by the electrophoretic flow of these solutions into the hair. The result is to increase the therapeutic effect of treatments for the hair including hair growth and regeneration. Other results include the even and stable dyeing of hair due to the increased adhering properties created through the electrophoretic device and the solutions used with it. These solutions include, but are not limited to, those dyeing and therapeutic agents which do not readily stick to the hair or those which may form unstable compounds.

6 Claims, 2 Drawing Sheets

ELECTROPHORETIC APPARATUS AND METHOD FOR APPLYING THERAPEUTIC, COSMETIC AND DYEING SOLUTIONS TO HAIR

This is a divisional of application Ser. No. 08/369,446 filed Jan. 6, 1995 now U.S. Pat. No. 5,472,456.

FIELD OF THE INVENTION

The present invention relates generally to dyeing solutions and methods of applying same to hair, and more specifically, to an apparatus and method of applying dyeing solutions, as well as other cosmetic and therapeutic solutions, to hair or skin. For hair dyeing, an electrophoretic comb is used to cause melanin to fixedly adhere to hair.

BACKGROUND OF THE INVENTION

Melanin is a naturally occurring coloring matter, and is found as a chromoprotein in hair, dark skins, certain insects and plants. With age, the body produces less melanin, and as a result, hair turns grey or white.

In the past, melanin has been applied to hair as a dyeing agent. An example can be found in U.S. Pat. No. 5,273,550 to Prota et al., in which an aqueous composition containing 5,6-dihydroxyindole (DHI) is applied to the hair, and the DHI diffuses into the hair shaft and turns into melanin via a dopa-oxidant reaction.

Other hair dyeing techniques and solutions are typically based on the use of harsh chemicals. For example, U.S. Pat. No. 4,453,941 to Jacobs et al. describes a method of dyeing hair using N-acetyl-dopamin and omega-amino acid. The hair was wetted with N-acetyldopamine and beta-alanin solutions.

U.S. Pat. No. 4,775,527 to Bires et al. describes the use of an aqueous preparation on the basis of melanin dissolution and/or oxidation of a hair colorant dye intermediate, which contains as a swelling and penetration agent an N-alkyl pyrrolidone with different alkyl groups.

U.S. Pat. No. 4,834,767 to Helioff et al. describes another example of a hair dyeing process using a swelling and penetration agent. The agent of choice is a quaternized amino lactam.

U.S. Pat. No. 5,173,085 to Brown et al. shows the prolonged formation of melanin from 5,6-dihydroxindole used with the subsequent use of hydrogen peroxide solution and oxidizing in air.

U.S. Pat. No. 5,279,618 to Prota et al. teaches a combination of dopa, oxidant and couplers, which improve and speed up the process of hair dyeing., Many of the foregoing references describe methods of hair dyeing that are based on the natural process of melanin developing from its precursors containing several dozens of chemical compounds. However, the concentration of dyeing agents, which would be enough for diffusion of dyeing agents is formed slowly. Thus, these methods are time consuming, and only the use of the ions of transitory metals and the strong oxidants might slightly accelerate it. Moreover, the use of mixtures, including the active oxidants, can be harmful to the hair.

There have been a variety of devices developed over the years for introducing treatment solutions to the hair and scalp. Representative examples include U.S. Pat. No. 4,090,522 to Donley et al. and U.S. Pat. No. 4,691,720 to Schmitz. In the former, a comb is provided with fluid-communicating teeth for applying a medication to the scalp. Fluid flow is by gravity. In the latter, a comb is used for applying dye to hair.

In some cases, electric devices have been used to apply an electric field to the scalp. U.S. Pat. No. 1,099,062 to Laposkey describes a device in which an electric current is induced in the scalp of the user. U.S. Pat. No. 1,724,984 to Wildey describes a comb having two rows of teeth that are electrically coupled to opposite terminals of a battery. A light bulb is connected between the rows of teeth.

In none of the above references has it been suggested how to affix an environmentally safe, naturally occurring dyeing agent to hair on a relatively long term basis.

SUMMARY OF THE INVENTION

An object of the present invention is to provide a method and apparatus for dyeing hair in which the number of chemicals is minimized.

Another object of the present invention is to provide a method and apparatus for dyeing hair in which the active dyeing agent is a naturally occurring substance.

Another object of the present invention is to provide a method and apparatus for dyeing hair in which the dyeing effect is substantially permanent.

A further object of the present invention is to provide an electrophoretic method and apparatus for applying therapeutic, cosmetic, and/or dyeing agents to various anatomical sites, especially human hair.

Still another object of the present invention is to minimize, or even exclude, the use of harmful oxidants, such as hydrogen peroxide, in a hair dyeing process.

These and other objects are achieved by providing a method of dyeing hair which includes the steps of applying a solution containing a dyeing agent to hair, and generating an electric field within the hair so as to induce flow and coupling of the dyeing agent to the hair by electrophoresis.

In another aspect of the present invention, an apparatus for dyeing hair includes a plurality of teeth coupled to a voltage source, alternating ones of the teeth having opposite polarity to establish localized electric fields within which a dyeing agent, cosmetic agent, and/or a therapeutic agent is induced to flow and couple to a variety of anatomical sites, such as hair.

Other objects, advantages and salient features of the invention will become apparent from the following detailed description, which, taken in conjunction with the annexed drawings, discloses preferred but non-limiting embodiments of the invention.

DETAILED DESCRIPTION OF THE INVENTION

Figure 1:
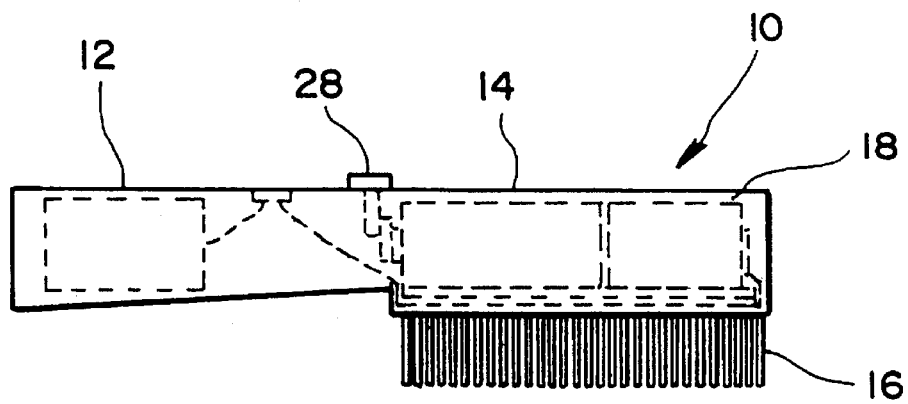
FIG. 1 is a side elevational view of an apparatus for electrophoretically applying a therapeutic, cosmetic, and/or hair dyeing agent, according to the present invention.

The present invention relies on electrophoresis to cause a therapeutic, cosmetic or dyeing agent to couple to an anatomical site, such as hair. In electrophoresis, electric current is not applied for direct action upon the skin and hair. Instead, it creates a flow of electrically charged particles of medication or dyeing agents into the hair or skin. The creation of a directed particles flow in the electric field facilitates the method of dyeing hair using the natural high molecular melanin. While entering into skin and hair, the electrically charged particles join those components of biological tissues, which had opposite charge, thus becoming electro-neutral and stopping the continued flow of the solutions in the electric field.

The prior art used diffusion in hair dyeing methods. Diffusion involves the disorderly thermal motion of molecules. When using this method, the fluid motion of medication and dying compounds will take a chaotic diversified character. At any given moment only a slight portion of these particles will be moving in a direction of the object, such as skin or hair. At the same time a certain quantity of these particles will diffuse back into the solution. For this reason, it will be necessary to use high concentrations of active agents.

Although electrophoresis has been known for some time, its use has been principally in the area of clinical analyses of proteins in diseases, genetics, and criminalistics for the separation of nucleotides. This method is widely used in industry to separate different compounds from impurities.

Pursuant to the present invention, the separation aspect of electrophoresis is used to introduce treatment and cosmetic solutions into hair or skin. The dyeing agents, for example, are separated from its transport fluid medium and induced to enter into the tissue space of the hair.

In order to enhance the effectiveness of diffusion processes, others have used heating sources. However, in the cosmetic field, heating is very limited because of the properties of living systems. In general, high temperatures harm the living tissues.

In certain cases compounds have natural electrical charges. However, if the compounds do not have electrical charges, through electrophoresis one can create an electrical charge by modifying the compounds or combine compounds that are electrically charged. In other words, if the necessary compounds do not have electrical charge, such a charge might be formed artificially using chemical modifications of the compounds.

Moreover, there are many ampholytic compounds having positive and negative charges. By suppressing the cationic or anionic dissociation in the medium, the oppositely charged particles are now becoming activated. When such compounds in the solution are placed within the conductivity and the electrical charge is on, the negatively charged particles start to flow towards the positive pole, or anode, and the positively charged towards the negative pole, or cathode.

General Procedure

Melanin was placed in a buffered solution having a pH in the range of 7.5 to 10 for melanin of plant origin and for Lipomelanin, and a pH of 6 to 7 for the low molecular genetic melanin. The solution is then applied to the hair liberally.

Figure 2:
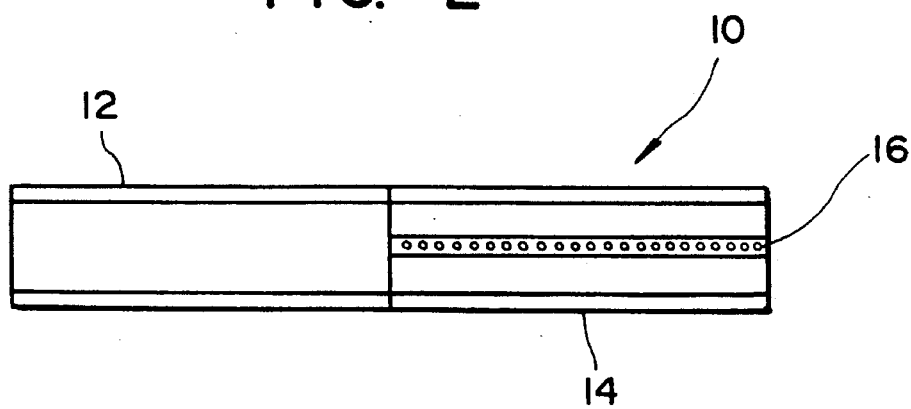
FIG. 2 is a bottom view of the apparatus of FIG. 1.
Figure 3:
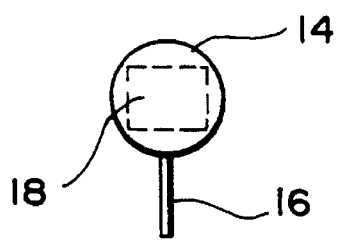
FIG. 3 is a front view of the apparatus of FIG. 1.

An electrophoretic device is then used to cause the melanin solution to migrate and couple to hair. Referring to FIGS. 1–3, an electrophoretic device 10 includes a handle portion 12 and an integrally formed body portion 14. The body portion supports a row of electrically conductive, spaced apart teeth 16.

The teeth 16 are coupled to a battery power source 18 disposed within either or both of the handle and body portions 12 and 14. The teeth are coupled so that every other one of the teeth is coupled to one pole of the battery and the remaining teeth are coupled to the opposite pole, so that alternating ones of the teeth have opposite polarity.

Figure 4:
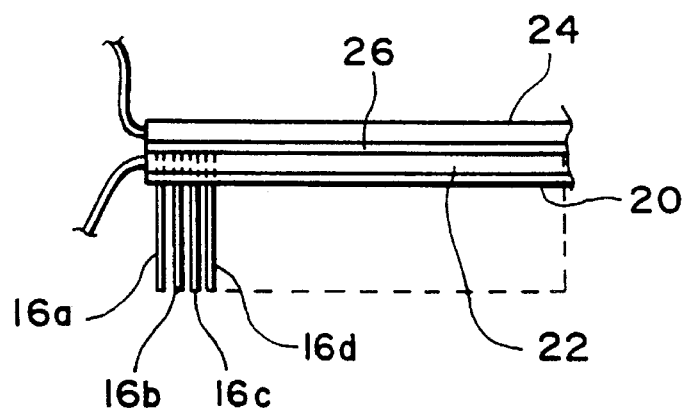
FIG. 4 is a side elevational view of the teeth and supporting structure of the apparatus of FIG. 1.

As seen in FIG. 4, the teeth 16 are insulated from each other at their proximal ends by an insulating strip 20. Every other tooth, including teeth 16a and 16b, are electrically interconnected by a conductive bar 22, which is then electrically connected to one of the terminals of the battery power source 18. For example, if the bar 22 is coupled to the positive terminal, then the teeth coupled thereto, including teeth 16a and 16b, will be positively charged.

The other teeth, including teeth 16b and 16d, are mounted on a second conductive bar 24 which is electrically isolated from conductive bar 22 by a strip 26 of insulating material. As the teeth coupled to bar 24 pass through the bar 22, they preferably pass through insulators so that the teeth mounted on bar 24 do not contact the bar 22. Bar 24 is electrically coupled to the other terminal of the battery power supply. For example, with bar 22 coupled to the positive terminal, bar 24 would be coupled to the negative terminal, so that the teeth mounted on bar 24 are negatively charged.

The battery power source can provide a range of voltages. It has been discovered that there exists a functional correlation between voltage and hair coloration, such that darker hair color can be obtained with higher voltages. Generally, voltages can range from 0.1 to 50 volts. Higher voltage may have a coloration effect, but have been avoided for safety reasons. The best results are in the range of 5 to 25 volts. Amperages range from 0.005 mA to 0.900 mA, with best results between 0.01 and 0.10 mA.

Figure 5:
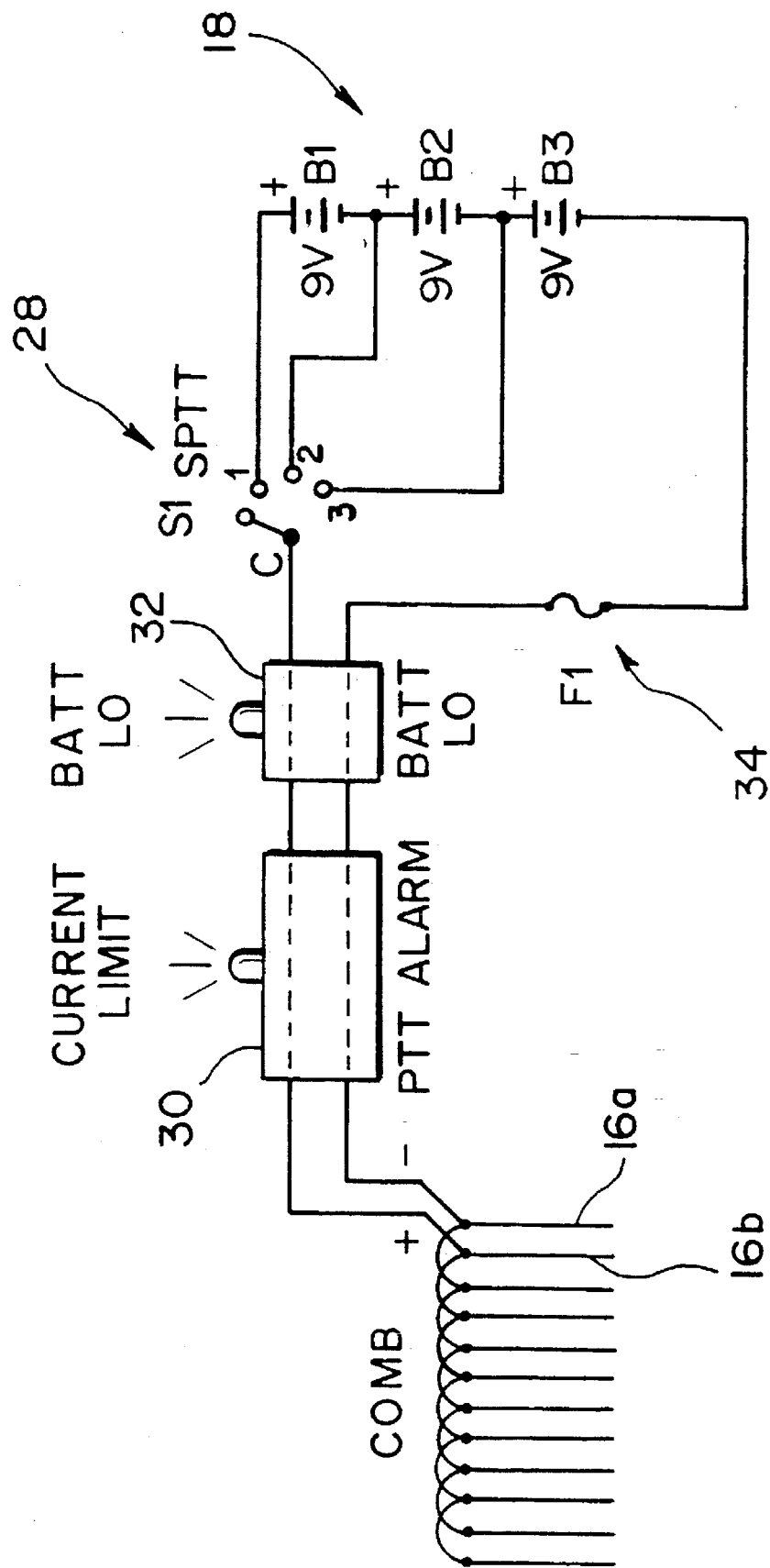
FIG. 5 is a wiring schematic of the apparatus of FIG. 1.

Referring to FIG. 5, the battery power source 18 includes three series connected 9 volt batteries B1, B2, and B3. A three-way switch 28 connects the power supply to the comb either at 9, 18, or 27 volts, depending on the desired effect. Additional optional components of the circuit include a current limit indicator 30, a battery low indicator 32, and a fuse 34.

Test Results

Various compounds were tested for their electrophoretic mobility, the speed and direction of the compounds. To determine the flow of compounds, free electrophoresis, i.e., in solution, can be used. In addition, other supporting media can be used, such as paper, cellulose acetate, starch, polyacrylamide, etc.

The tested component is spread upon the medium and the direct current is switched on. After the appropriate time, and, if necessary, after the dyeing process, the direction and the distance is calculated. Based on this data the time necessary for the procedure is determined.

The choice of buffer medium depends upon several events. The following conditions must be taken into consideration: (1) the highest mobility of the component, (2) the absence of harmful ingredients in the buffer, and (3) the physiologically available limits of pH.

For compounds having no charge, i.e., electro-neutral, a chemical modification might be used, which forms such a charge, or they might be additionally joined to the charged molecule.

In case the hair possesses a very strong keratin cuticle, which prevents the electrophoresis, chemical compounds capable of destroying the S—S bonds or the relative enzymes might be used.

Solutions

All examples that follow describe a solution containing an active agent, such as melanin, and a buffer. The buffer can be any of a variety of commercially available buffers, which may include water, phosphates and acetates. The ranges of active agents are measured as weight/volume (such as 10 grams of melanin per 100 ml of buffer). Also, for melanin, it is preferred to add about 2 to 3 cc of ammonia per 100 ml of buffer.

Example I

A hair dyeing solution using human melanin was tested. The preliminary test with electrophoresis in agarose shows that this melanin is moving in alkali medium in an electric field in the direction of the anode. The solution, containing melanin, is spread upon hair and is combed with an electrophoretic device. The period of this process determines the desired color or tint.

While using a 0.5% solution of melanin in a buffer up to pH 8, a medium golden tint of hair is achieved in about five minutes.

Example II

A hair dyeing solution using plant melanin was tested. The preliminary electrophoretic test has shown the motion of such melanin molecules towards the anode. The hair dyeing process was the same as in Example I. Virgin hair was used in different concentrations of melanin from 0.5% to 10%. The results were as follows:

| Concentration | Hair Color |
| --- | --- |
| 0.5% | light golden |
| 1.5% | dark golden |
| 3.0% | brown |
| 5.0% | dark brown |
| 10% | brunette |

Example III

In this example, the electrophoretic device of the present invention was used with commercially available melanins produced by Lipo Chemical Company and genetic companies such as BioSource Technologies, Inc. The hair was preliminarily processed with oxidants or keratininase solution in order to weaken the cuticle layer and make the hair medulla available.

Similar techniques to those discussed in Example I were used to apply the melanin-containing solution, and comparable coloration was achieved.

Example IV

Hair dyeing with catecholamine (pyrocatechine) derivatives described in the prior art patents was performed, except without the recommended oxidants, but using the electrophoretic methods described herein. Results were comparable to those mentioned above.

Example V

The same method as that used in Example IV was used with the dyes of diphenylamine-row, with satisfactory results.

The use of electrophoresis and most importantly the use of the electrophoretic device described hereinbelow solves the adhesion problem by enabling the hair to absorb various solutions through the directed flow of electrically charged particles in normal conditions and without the need for increased temperatures.

In addition to the aforementioned use of electrophoresis with hair, it is also noted that there is an electrochemical process that occurs on positive and negative electrodes. In particular, the effusion of the oxygen upon the electrodes can be used for the oxidation of commercial hair dyes. This would eliminate the use of chemical oxidants such as hydrogen peroxide and persulphates.

While advantageous embodiments have been chosen to illustrate the subject invention, it will be understood by those skilled in the art that various changes and modifications can be made therein without departing from the scope of the invention as defined by the appended claims.

We claim:

1. A system for applying a dyeing agent to hair comprising:

a solution containing a dyeing agent capable of being applied to the hair;

a plurality of positive electrodes;

a plurality of negative electrodes juxtaposed the positive electrodes so as to establish an electric field therebetween; and a voltage supply coupled to the positive and negative electrodes, and having a voltage level sufficient to impart electrophoretic motion of the dyeing agent into the hair.

2. A system according to claim 1, wherein the voltage supply comprises at least three series connected batteries and a switch selectively connecting the positive and negative electrodes to at least one of the at least three batteries.

3. A system according to claim 1, wherein the electrodes are arranged in the form of a comb.

4. A system according to claim 1, further comprising a body having a handle portion and a head portion supporting the plurality of positive and negative electrodes.

5. A system according to claim 4, wherein the voltage supply comprises at least one battery disposed within the body.

6. A system for applying a dyeing agent to hair comprising:

a solution containing a dyeing agent capable of being applied to the hair;

a comb having a plurality of teeth; and a voltage supply electrically connected to the teeth in a manner capable of forming an electric field between the teeth, the solution being disposed in the electric field so as to impart electrophoretic motion of the dyeing agent into the hair.

* * * * *